(12) United States Patent
Bastings et al.

(10) Patent No.: US 11,655,230 B2
(45) Date of Patent: May 23, 2023

(54) PROCESS FOR PREPARING ETHYLENE CARBONATE AND ETHYLENE GLYCOL USING AN ALKYL IODIDE GUARD BED SYSTEM

(71) Applicant: SHELL OIL COMPANY, Houston, TX (US)

(72) Inventors: Roel Guillaume Hubertus Leonardus Bastings, Amsterdam (NL); Jesse Raymond Black, Houston, TX (US); Vesna Bojovic, Ras Laffan (QA); Wayne Errol Evans, Houston, TX (US)

(73) Assignee: SHELL USA, INC., Houston, TX (US)

( * ) Notice: Subject to any disclaimer, the term of this patent is extended or adjusted under 35 U.S.C. 154(b) by 369 days.

(21) Appl. No.: 16/769,557

(22) PCT Filed: Dec. 6, 2018

(86) PCT No.: PCT/EP2018/083755
§ 371 (c)(1),
(2) Date: Jun. 3, 2020

(87) PCT Pub. No.: WO2019/110716
PCT Pub. Date: Jun. 13, 2019

(65) Prior Publication Data
US 2020/0392101 A1    Dec. 17, 2020

(30) Foreign Application Priority Data

Dec. 8, 2017 (EP) .................... 17206145

(51) Int. Cl.
*C07D 317/38* (2006.01)
*C07C 29/17* (2006.01)

(52) U.S. Cl.
CPC .......... *C07D 317/38* (2013.01); *C07C 29/172* (2013.01)

(58) Field of Classification Search
CPC ............................ C07D 317/38; C07C 29/172
USPC ........................................................ 549/449
See application file for complete search history.

(56) References Cited

U.S. PATENT DOCUMENTS

2009/0286998 A1    11/2009    Evans et al.

FOREIGN PATENT DOCUMENTS

| | | |
|---|---|---|
| EP | 0776890 A2 | 6/1997 |
| GB | 2107712 A | 5/1983 |
| WO | 2008144402 A2 | 11/2008 |
| WO | 2009021830 A1 | 2/2009 |
| WO | 2009140318 A1 | 11/2009 |
| WO | 2016046100 A1 | 3/2016 |
| WO | 2017102694 A1 | 6/2017 |
| WO | 2017102698 A1 | 6/2017 |
| WO | 2017102701 A1 | 6/2017 |
| WO | 2017102706 A1 | 6/2017 |

OTHER PUBLICATIONS

International Search Report and Written Opinion received for PCT Patent Application No. PCT/EP2018/083755, dated Mar. 7, 2019, 10 pages.
Brunauer et al., "Adsorption of Gases in Multimolecular Layers", Journal of the American Chemical Society, vol. 60, Issue No. 2, Feb. 1938, pp. 309-319.

*Primary Examiner* — Kristin A Vajda
(74) *Attorney, Agent, or Firm* — Shell USA, Inc.

(57) ABSTRACT

The invention relates to a process for producing ethylene glycol and/or ethylene carbonate, said process comprising contacting at least a portion of a recycle gas stream comprising an alkyl iodide impurity with a guard bed system positioned upstream of an ethylene oxide reactor to produce a treated recycle gas stream, wherein the guard bed system comprises silver on alumina; contacting a feed gas stream comprising ethylene, oxygen and at least a portion of the treated recycle gas stream with an epoxidation catalyst in the ethylene oxide reactor to produce an epoxidation reaction product comprising ethylene oxide; and contacting at least a portion of the epoxidation reaction product comprising ethylene oxide with an aqueous absorbent in the presence of an iodide-containing catalyst in an absorber to produce an aqueous product stream comprising ethylene carbonate and/or ethylene glycol and the recycle gas stream comprising the alkyl iodide impurity.

5 Claims, 1 Drawing Sheet

PROCESS FOR PREPARING ETHYLENE CARBONATE AND ETHYLENE GLYCOL USING AN ALKYL IODIDE GUARD BED SYSTEM

CROSS REFERENCE TO RELATED APPLICATIONS

This is a national stage application of International application No. PCT/EP2018/083755, filed 6 Dec. 2018, which claims priority of European application No. 17206145.9, filed 8 Dec. 2017.

FIELD OF THE INVENTION

The present invention relates to a process for the preparation of ethylene oxide, ethylene carbonate and/or ethylene glycol from ethylene, in particular where such process uses a guard bed for removing alkyl iodide impurities from a recycle gas stream.

BACKGROUND OF THE INVENTION

Ethylene glycol (EG) is a valuable industrial compound that is widely employed as starting material for the manufacture of polyester fibers and polyethylene terephthalate (PET) resins; it also finds application in automotive antifreeze and hydraulic brake fluids, aircraft de-icers as well as in pharmaceutical products.

Ethylene glycol is normally prepared from ethylene oxide (EO). Ethylene oxide is in turn prepared by silver-catalyzed oxidation of ethylene. More specifically, ethylene and oxygen are passed over a silver oxide catalyst, typically at pressures of 10-30 bar and temperatures of 200-300° C., producing a product stream comprising ethylene oxide, carbon dioxide, ethylene, oxygen, and water. In one well-known process, the ethylene oxide is then reacted with a large excess of water in a non-catalytic process, producing a glycol product stream comprising close to 90 wt % monoethylene glycol (MEG), the remainder being predominantly diethylene glycol (DEG), some triethylene glycol (TEG) and a small amount of higher homologues. In another well-known process, ethylene oxide is reacted with carbon dioxide in the presence of a catalyst to produce ethylene carbonate. The ethylene carbonate is subsequently hydrolyzed to provide ethylene glycol. Reaction via ethylene carbonate significantly improves the selectivity of ethylene oxide conversion to monoethylene glycol.

In the last few decades, many efforts have been directed towards the development of simplified processes and equipment for producing alkylene glycols from alkylenes, notably ethylene glycol from ethylene. For example, GB2107712 describes a process for preparing monoethylene glycol wherein the gases from the ethylene oxide (EO) reactor are supplied directly to a reactor wherein ethylene oxide is converted to ethylene carbonate or to a mixture of ethylene glycol and ethylene carbonate.

EP 0776890 describes a process wherein the gases from the ethylene oxide reactor are supplied to an ethylene oxide absorber, wherein the absorbing solution mainly contains ethylene carbonate (EC) and ethylene glycol (EG). The ethylene oxide in the absorbing solution is supplied to a carboxylation reactor and allowed to react with carbon dioxide in the presence of a carboxylation catalyst. The ethylene carbonate in the absorbing solution is subsequently supplied, with the addition of water, to a hydrolysis reactor and subjected to hydrolysis in the presence of a hydrolysis catalyst.

EP2178815 describes a reactive absorption process for preparing monoethylene glycol, wherein the gases from the ethylene oxide reactor are supplied to a reactive absorber and the ethylene oxide is contacted with an aqueous lean absorbent in the presence of one or more carboxylation and hydrolysis catalysts, and wherein the majority of the ethylene oxide is converted to ethylene carbonate (EC) or ethylene glycol (EG) in the absorber.

In each of these cases, a gas stream containing gases that are not absorbed by the recirculating absorbent stream will be produced from the absorber. This gas stream is treated in a carbon dioxide absorption column and then recombined with any gases bypassing the carbon dioxide absorption column. The combined gases are then at least partially recycled, as recycle gas stream, to the EO reactor.

However, it has been found that in those processes where the carboxylation reaction is performed in a reactive absorber using an iodide-containing carboxylation catalyst, decomposition materials and side products may be present in the recycle gas stream and/or in the fat absorbent stream. Examples of such decomposition materials and side products include gaseous iodide-containing impurities, such as alkyl iodides (e.g., methyl iodide, ethyl iodide, etc.) and vinyl iodide.

The silver-based catalysts commonly employed in the conversion (epoxidation) of ethylene to ethylene oxide are very susceptible to catalyst poisoning, in particular poisoning by gaseous iodide-containing impurities, such as alkyl iodides and vinyl iodide. Catalyst poisoning impacts the epoxidation catalyst performance, in particular the selectivity and/or the activity, and shortens the length of time the epoxidation catalyst can remain in the epoxidation reactor before it becomes necessary to exchange the catalyst with fresh catalyst.

Accordingly, it is desirable to remove such catalyst poisons as much as is practicable from the recycle gas stream before it comes into contact with the epoxidation catalyst. To this end, various so-called "guard bed systems" positioned upstream of the EO reactor, as previously disclosed in, among others, EP2285795, EP2279182 and EP2155375 have been developed. Such guard bed systems typically comprise one or more vessels, each guard bed vessel comprising an inlet, an outlet, and a packed bed ("guard bed") comprising an absorbent ("guard bed material") capable of reducing the quantity of iodide-containing impurities in a fluid stream by chemical or physical means including, but not limited to, reaction with the impurities and absorption/adsorption of the impurities.

During operation, the guard beds become increasingly exhausted as a result of the continuous removal of iodide-containing impurities from the recycle gas stream, leading to a loss of capacity for impurities removal compared to the guard bed's initial capacity. Such loss of capacity leading to the bed letting through unacceptable levels of impurities is referred to as "breakthrough" and, if no proper adjustments are made to the guard bed design (i.e., increased adsorbent volume) to forestall these losses, necessitates refreshing the guard bed system by partially or entirely removing the guard bed material and replacing it with fresh or re-activated guard bed material.

In a characteristic set-up, a first guard bed is on-line while a second guard bed is kept stand-by and switched on as soon as the first guard bed needs to be refreshed, until the second guard bed (with the refreshed first bed stand-by) becomes exhausted and the process is repeated.

Typically, in such a simple guard bed arrangement, the guard bed material is only partially used up when the amount of iodide-containing impurities passing through the guard bed vessel will already have risen to unacceptable levels. In an effort to enhance the utilization of expensive guard bed material, very recently more advanced guard bed system arrangements have been developed, wherein an iodide-contaminated gaseous stream is fed through a guard bed system comprising a connected array of guard bed vessels, and wherein the first guard bed vessel in line upon becoming exhausted is refreshed and subsequently reinserted and used as the last guard vessel bed in line in a merry-go-round-like fashion as disclosed in WO2017/102694.

There are many factors that affect the capacity of guard bed systems to effectively reduce the quantity of iodide-containing impurities in the recycle gas stream and thus preventing poisoning of the EO catalyst. Among these factors is the presence in the recycle gas, besides the vinyl and/or alkyl iodide impurities, of other reactants, reaction products, and/or by-products which by itself or in combination influence the guard bed capacity.

It has been found now that in particular the presence of water and/or ethylene oxide above certain levels causes a decline in the capacity for removing alkyl iodide impurities from the recycle gas stream of guard bed systems configured for removing alkyl iodide impurities.

Accordingly, it is imperative that the ethylene oxide/ethylene glycol process design takes into account controlling the levels of components of the recycle gas stream that affect guard bed capacity as well as proper compensation for anticipated loss of guard bed volume during the entire lifecycle of the epoxidation catalyst.

Thus, a need has arisen for an improved process for preparation of ethylene oxide, ethylene carbonate and/or ethylene glycol from ethylene, in particular a process that uses a guard bed system for removing alkyl iodide impurities from a recycle gas stream upstream of an ethylene oxide reactor.

SUMMARY OF THE INVENTION

Accordingly, in a first aspect, the present invention provides a process for producing ethylene glycol and/or ethylene carbonate, said process comprising contacting at least a portion of a recycle gas stream comprising an alkyl iodide impurity with a guard bed system positioned upstream of an ethylene oxide reactor to produce a treated recycle gas stream, wherein said guard bed system comprises a guard bed material comprising silver on alumina;

contacting a feed gas stream comprising ethylene, oxygen and at least a portion of the treated recycle gas stream with an epoxidation catalyst in the ethylene oxide reactor to produce an epoxidation reaction product comprising ethylene oxide; and contacting at least a portion of the epoxidation reaction product comprising ethylene oxide with an aqueous absorbent in the presence of an iodide-containing catalyst in an absorber to produce an aqueous product stream comprising ethylene carbonate and/or ethylene glycol and the recycle gas stream comprising the alkyl iodide impurity, wherein the recycle gas stream supplied to the guard bed system comprises (a) no more than 0.6 mol % of water; and/or (b) no more than 90 ppmv of ethylene oxide, based on total recycle gas stream supplied to the guard bed system.

DETAILED DESCRIPTION OF THE INVENTION

Figure 1:
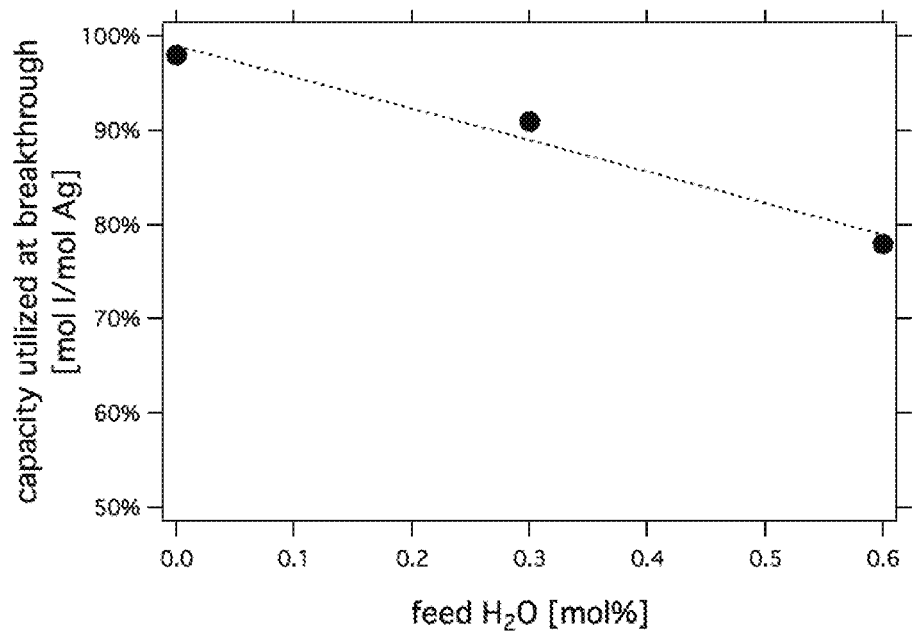
FIG. 1 shows the effect of water in an ethylene epoxidation feed gas stream on the iodide sorption capacity of a silver-based guard bed.

The present invention provides a process for controlling the capacity of a guard bed system positioned upstream of a catalytic EO reactor used in a process for producing ethylene glycol and/or ethylene carbonate.

The process of producing ethylene glycol and/or ethylene carbonate by epoxidation of ethylene and reactive absorption of ethylene oxide has been described in detail in, among others, WO2009021830, WO2009140318, WO2009140319, their disclosure incorporated herein by reference. Specifically, guard bed systems for use in this process have been described in detail in WO2008144402, WO2017102694, WO2017102698, WO2017102701 and WO2017102706.

Typically, this process comprises reacting, in an ethylene oxide reactor, ethylene with oxygen in the presence of an epoxidation catalyst to form ethylene oxide. In such a reaction, the oxygen may be supplied as oxygen or as air, but is preferably supplied as oxygen. Ballast gas, for example methane or nitrogen, is typically supplied to allow operation at high oxygen levels without causing a flammable mixture. Moderator, e.g. monochloroethane (ethyl chloride), vinyl chloride or dichloroethane, may be supplied for ethylene oxide catalyst performance control. The ethylene, oxygen, ballast gas and moderator are preferably supplied to recycle gas that is supplied to the ethylene oxide reactor from an ethylene oxide absorber (preferably via a carbon dioxide absorption column). The catalyst is preferably finely dispersed silver and optionally promoter metals on a support material, for example, alumina. The reaction is preferably carried out at pressures of greater than 1 MPa and less than 3 MPa and temperatures of greater than 200° C. and less than 300° C. The gas composition from the ethylene oxide reactor is preferably cooled in one or more coolers, preferably with generation of steam at one or more temperature levels.

The gas composition is then passed to a reactive absorber in which it is intimately contacted with lean absorbent. The lean absorbent typically comprises at least 20 wt % water, preferably from 20 wt % to 80 wt % water. Preferably, the lean absorbent also comprises ethylene carbonate and/or ethylene glycol. At least a portion of, and preferably substantially all of the ethylene oxide in the gas composition is absorbed into the lean absorbent. In accordance with the present invention, the gas composition is intimately contacted with the lean absorbent in the presence of one or more catalysts that promote carboxylation and hydrolysis. Suitably, the absorber may be the sort of reactive absorber described in WO2009021830 or in WO2016046100. Preferred homogeneous catalysts that are known to promote carboxylation include alkali metal iodides such as potassium iodide and halogenated organic phosphonium or ammonium salts such as tributylmethylphosphonium iodide, tetrabutylphosphonium iodide, triphenylmethylphosphonium iodide and tributylmethylammonium iodide. Homogeneous catalysts that are known to promote hydrolysis include basic alkali metal salts such as potassium carbonate, potassium hydroxide and potassium bicarbonate, or alkali metal metalates such as potassium molybdate.

Preferred homogeneous catalyst systems include a combination of potassium iodide and potassium carbonate, and a combination of potassium iodide and potassium molybdate. Heterogeneous catalysts that promote carboxylation include quaternary ammonium and quaternary phosphonium iodides immobilized on silica, quaternary ammonium and quaternary phosphonium iodides bound to insoluble polystyrene beads, and metal (e.g. zinc) iodides, immobilised on solid supports containing quaternary ammonium or quaternary phosphonium groups, such as ion exchange resins containing quaternary ammonium or quaternary phosphonium groups. Heterogeneous catalysts that promote hydrolysis include metalates immobilised on solid supports, for example molybdates, vanadates or tungstates immobilised on ion exchange resins containing quaternary ammonium or quaternary phosphonium groups, or basic anions such as bicarbonate ions immobilised on solid supports, for example bicarbonate immobilised on ion exchange resins containing quaternary ammonium or quaternary phosphonium groups.

A 'fat absorbent' stream is withdrawn from the absorber, preferably by withdrawing liquid from the bottom of the absorber. The fat absorbent stream will contain ethylene carbonate and/or ethylene glycol and any remaining EO, if present, depending on the conditions, set-up and catalyst in the absorber.

Any gases that are not absorbed in the absorber, including any catalyst decomposition products or side products, are removed from the top of the absorber and are ultimately recycled to the epoxidation reactor. Preferably, at least a portion of the gas to be recycled to the epoxidation reactor will be supplied to a carbon dioxide absorption column, wherein carbon dioxide is at least partially absorbed, before the thus-treated gas is supplied to the epoxidation reactor.

The present inventors have found that in particular organic iodide-containing impurities, and more in particular vinyl iodide and alkyl iodides such as ethyl and methyl iodide, in the recycle gas need to be reduced to very low levels in order for the performance of the epoxidation catalyst to remain unaffected by their presence.
In particular, the amount of alkyl iodide present in a partially treated recycle gas stream is preferably no more than 6 ppbv, more preferably no more than 5 ppbv, even more preferably no more than 3 ppbv, even more preferably no more than 2 ppbv, and most preferably no more than 1 ppbv. Further, the amount of vinyl iodide present in a treated recycle gas stream is preferably no more than 20 ppbv, preferably no more than 15 ppbv, preferably no more than 10 ppbv, more preferably no more than 5 ppbv, even more preferably no more than 4 ppbv, even more preferably no more than 3 ppbv, and most preferably no more than 1 ppbv. Similarly, the total amount of alkyl iodide and vinyl iodide present in a treated recycle gas stream supplied to the epoxidation reactor is preferably no more than 26 ppbv, preferably no more than 20 ppbv, preferably no more than 16 ppbv, preferably no more than 13 ppbv, preferably no more than 10 ppbv, more preferably no more than 7 ppbv, even more preferably no more than 5 ppbv, most preferably no more than 2 ppbv.

Such very low levels of iodide impurities in the recycle gas stream from the EO absorber supplied to the ethylene oxide (EO) reactor are obtainable by the use of one or more guard bed systems positioned upstream of the EO reactor. Within such a guard bed system, the recycle gas stream passes through one or more, preferably two or more guard bed vessels and is contacted with the guard bed material in each guard bed vessel, whereby impurities, typically one or more iodide impurities, are at least partially removed. Depending on the impurities content of the gaseous feed, impurities will be removed in the first guard bed vessel and, possibly, any further guard bed vessel. A treated gaseous feed will be removed from the guard bed system. Said treated gaseous feed will have a reduced level of impurities.

As used herein, at least one of the guard bed materials is a silver on alumina-based support material. This type of guard bed material is particularly suited for removing alkyl iodide impurities, in particular methyl iodide and ethyl iodide, from the recycle gas stream. Suitably, the guard bed material capable of removing one or more alkyl iodide impurities from the recycle gas stream comprises an alumina support material, and deposited on the alumina support material, silver in an amount of from 2% to 10% by weight. A small amount of potassium carbonate ($K_2CO_3$) is used to passivate the alumina and enhance the uptake of iodine. Preferably, the first support material comprises gamma-alumina. A suitable support material may have a surface area of more than 20 $m^2/g$, relative to the weight of the support material, or at least 25 $m^2/g$, or at least 50 $m^2/g$, or at least 75 $m^2/g$, or at least 100 $m^2/g$, or at least 125 $m^2/g$, or at most 1200 $m^2/g$, or at most 500 $m^2/g$, or at most 300 $m^2/g$, or at most 200 $m^2/g$, or at most 175 $m^2/g$, or from 20 $m^2/g$ to 1200 $m^2/g$, or from 50 $m^2/g$ to 500 $m^2/g$, or from 75 $m^2/g$ to 300 $m^2/g$, or from 100 $m^2/g$ to 200 $m^2/g$, or from 125 $m^2/g$ to 175 $m^2/g$, on the same basis. As used herein, "surface area" is understood to refer to the surface area of the support material as measured in accordance with the B.E.T. (Brunauer, Emmett and Teller) method as described in detail in Brunauer, S., Emmet, P. Y. and Teller, E., J. Am. Chem. Soc., 60, pgs. 309-316 (1938). Preferably, the alumina support material is a spherical support material and has a diameter of less than 2 mm, or 1.8 mm or less, or 1.6 mm or less, or 1.5 mm or less, or 1.3 mm or less, or 1.0 mm or less, or a diameter from 0.25 mm to less than 2 mm, or from 0.5 mm to less than 2 mm, or from 0.75 mm to less than 2 mm, or from 1 mm to less than 2 mm, or from 0.25 mm to 1.5 mm, or from 0.5 mm to 1.5 mm, or from 0.75 mm to 1.5 mm, or from 1 mm to 1.5 mm.

The one or more guard bed vessels comprising a silver on alumina-based guard bed material are preferably operated at a temperature of at least 100° C., more preferably at least 115° C., most preferably at least 120° C. In this embodiment, the one or more guard beds are preferably operated at a temperature of at most 145° C., more preferably at most 140° C., even more preferably at most 135° C., most preferably at most 130° C.

In some instances, the recycle gas stream passes through at least two guard bed systems, wherein a first guard bed systems is configured for removing one or more alkyl iodide impurities (such as methyl iodide and ethyl iodide) as described above to provide a partially treated recycle gas stream, wherein the partially treated recycle gas stream is subsequently provided to a second guard bed systems configured for removing one or more vinyl iodide impurities to provide a further treated recycle gas stream. Thus, in one embodiment, the recycle gas stream supplied to the guard bed system is further contacted with a second guard bed system comprising a guard bed material capable of removing at least a portion of a vinyl iodide impurity from the recycle gas stream, wherein the treated gaseous feed stream removed from the final guard bed vessel in series of the first guard bed system is supplied as the gaseous feed via a feed line to the second guard bed system.

A suitable guard bed material for removing vinyl iodide impurities from a recycle gas stream is a palladium/gold based material, preferably supported on silica. Thus, in one embodiment, the guard bed material capable of removing at least a portion of a vinyl iodide impurity comprises palladium and gold, preferably supported on silica. The use of such guard beds in a process for preparing ethylene carbonate and/or ethylene glycol has been described in detail in WO2017102701. In this embodiment, the one or more guard bed vessels comprising a palladium/gold based material are preferably operated at a temperature of at least 65° C., more preferably at least 70° C., most preferably at least 83° C. In this embodiment, the one or more guard bed vessels are preferably operated at a temperature of at most 95° C., more preferably at most 90° C., even more preferably at most 87° C., most preferably at most 85° C.

Preferably, the gaseous feed to be treated is recycle gas from a reactive absorber that has yet to be treated in a carbon dioxide absorption column. Positioning the guard bed system at this stage in the process may have the added advantage of protecting the $CO_2$ absorber from any potential effects that may be caused by the impurities that are removed by the guard bed system.

The feed line, optionally, contains one or more heating or cooling devices, such as heat exchangers, in order to alter the temperature of the gaseous feed to be optimal for the guard bed system.

Each bed of guard bed material may be contained within the guard bed vessel in any suitable system. Preferred systems include an axial fixed bed, wherein the gas to be treated is contacted with the bed of guard bed material as an axial flow, and a radial fixed bed, wherein the gas to be treated is supplied from the inlet to the outside of the fixed bed and passes through the fixed bed to the centre of the guard bed vessel and then to the outlet. A radial fixed bed is preferred, as such a bed generally will have a lower pressure drop.

In a preferred embodiment, two or more guard bed systems arranged in series are used, each guard bed system comprising one or more guard bed vessels arranged in sequential order. Herein, each guard bed vessel comprises an inlet, a bed of guard bed material and an outlet, wherein the inlet of each guard bed vessel is attached by means of valves to both the feed line and the outlet of the guard bed vessel preceding it in sequential order, wherein the outlet of each guard bed vessel is attached by means of valves to both the effluent line and to the inlet of the guard bed vessel following it in sequential order and wherein the guard bed vessel following the last guard bed vessel in sequential order is the first guard bed vessel in sequential order. In operation, once the amount of impurities in the gaseous feed leaving the first guard bed vessel in series approaches a pre-determined level, the guard bed vessel is removed from the flow of the gaseous feed by operation of valves. The flow of the gaseous feed continues through the second guard bed vessel and any subsequent guard bed vessels. The guard bed material in the first guard bed vessel is then replaced by fresh or reactivated material. Once the guard bed material in the first guard bed vessel is refreshed, flow of the gaseous feed through said guard bed vessel is restored by operation of valves. However, it is restored such that the first guard bed vessel is now the last guard bed vessel in series to be contacted with the gaseous feed. After a further period of time, again determined by monitoring of the level of impurities in the gaseous flow, the same steps are applied to the second guard bed vessel in series (which at this stage is contacted with the gaseous feed first), and so on. Guard bed systems of this type are described in detail in WO2017/102694. A particular advantage of operating the one or more guard bed systems in this rotating way is that a very high proportion of catalyst poison impurities present in the recycle gas are removed, while at the same time, the guard bed system is used in a reliable, efficient and economic manner.

In any embodiment, the pressure in each guard bed system will be determined by the pressure of the gas loop in the overall system. A preferable operating pressure is in the range of from 1 to 4 MPa (gauge). A more preferable operating pressure is in the range of from 2 to 3 MPa (gauge).

The theoretical capacity for a silver/potassium-based guard bed material is calculated from reaction stoichiometry assuming the formation of AgI(s) and KI(s). The governing formulae are $$\text{Molar Iodine Capacity} \left[\frac{kmol}{m^3}\right] = \frac{\rho_{bed}}{100} \cdot \left(\frac{w\% \, Ag}{MW_{Ag}} + \frac{w\% \, K}{MW_K}\right)$$

$$\text{Mass Iodine Capacity} \left[\frac{kg}{m^3}\right] = \text{Molar Iodine Capacity} \cdot MW_I$$

Herein, $\rho_{bed}$ represents the guard bed density (in kg/m³), and $MW_{Ag}$ and $MW_K$ are the molar weights (in mol/g) of silver and potassium, respectively.

The present inventors have found that if certain operating conditions of the ethylene oxide/ethylene glycol process are not properly controlled, the capacity of guard beds for removing iodide impurities from the recycle gas stream rapidly decreases, necessitating the addition of large volumes of surplus guard bed material to compensate for such capacity losses and/or high guard bed changeout frequencies, both of which are economically unattractive options.

The present inventors have developed design and operating strategies that minimize the amount of guard bed material that must be used to keep the ethylene oxide/ethylene glycol process running by protecting the epoxidation catalyst from alkyl iodides. Generally, this involves controlling the concentration of those components of the recycle gas stream that adversely affect guard bed capacity at minimum achievable levels. Furthermore, it involves adding well-defined amounts of guard bed material (bed sizing) to compensate for any capacity reductions expected whilst controlling the amount of adverse recycle gas components within specific boundaries.

It has been found by the present inventors that the performance of particularly the guard bed material in a guard bed system configured for removing alkyl iodide impurities is detrimentally affected by the presence of excess water in the recycle gas stream supplied to the guard bed system, with water reducing the capacity for removing iodide impurities in a substantially linear dependence. Typically, in the process of the invention, the water concentration in the recycle gas stream is controlled by one or more of the type of cooling medium, type of cooling apparatus, temperature of the cooling medium, and the amount of cooling medium used to cool the recycle gas stream leaving the absorber. If cooling water (e.g., of 40° C.) is applied this will lead to relatively higher water concentrations, whereas reduced water concentrations can be obtained by the use of more cost-intensive chilling machines operating on low pressure stream preferably generated elsewhere in the process, or electrical power.

In the present invention, the recycle gas stream supplied to the guard bed system may comprise water and the water amount in the recycle gas stream may be at most 0.6 mol %. In a preferred embodiment, the composition of the recycle gas stream supplied to the guard bed system is controlled such that it comprises no more than 0.59 mol % of water, more preferably no more than 0.55 mol % of water, more preferably no more than 0.5 mol % of water, more preferably no more than 0.4 mol % of water, more preferably no more than 0.3 mol % of water, even more preferably no more than 0.2 mol % of water, most preferably no more than 0.1 mol % of water. By controlling water concentration in the recycle gas stream within these limits, excessive adjustments to guard bed size and/or changeout frequency are avoided, thus contributing to optimized design and operation of the overall ethylene oxide/ethylene glycol process as described herein, and minimized capital and operating expenditure.

It was further found by the present inventors that the performance of the guard bed system is significantly affected by the presence of excess ethylene oxide (EO) in the recycle gas stream supplied to the guard bed system, with a rapid decrease in iodide reduction capacity of the guard bed system with increasing ethylene oxide concentration in the recycle feed gas stream. Excess ethylene oxide in the recycle gas stream originates from ethylene oxide produced in the ethylene oxide reactor that has not been fully absorbed by the recirculating absorbent stream in the EO absorber or reactive absorber. In the present invention, the recycle gas stream supplied to the guard bed system may comprise ethylene oxide and the ethylene oxide amount in the recycle gas stream may be at most 90 ppmv. Accordingly, in one embodiment of the invention, the composition of the recycle gas stream supplied to the guard bed system is controlled such that it comprises no more than 90 ppmv of ethylene oxide. In a preferred embodiment, the recycle gas stream supplied to the guard bed system comprises no more than 70 ppmv of ethylene oxide, more preferably no more than 50 ppmv of ethylene oxide, more preferably no more than 40 ppmv of ethylene oxide, more preferably no more than 30 ppmv of ethylene oxide, more preferably no more than 25 ppmv of ethylene oxide, more preferably no more than 20 ppmv of ethylene oxide, even more preferably no more than 15 ppmv of ethylene oxide, yet even more preferably no more than 10 ppmv of ethylene oxide, most preferably no more than 5 ppmv of ethylene oxide. In one embodiment, the composition of the recycle gas stream supplied to the guard bed system is controlled such that it comprises substantially no ethylene oxide, or no ethylene oxide.

Typically, ethylene oxide concentration in the recycle gas stream may be controlled by regulating ethylene oxide concentration in the epoxidation reaction product stream, temperature and/or pressure in the absorber, catalyst composition, the number and/or design of absorber trays, flow of absorbent in the absorber, and/or absorbent composition in the absorber.

By maintaining the concentration of water and/or ethylene oxide below the above-defined limits, any capacity loss of the guard bed system for removing alkyl iodide impurities from the recycle gas stream throughout the catalyst lifecycle is kept at levels that can be obviated by directed process design. More specifically, by operating the process as essentially described herein, the amount of additional guard bed material that should be used to protect the epoxidation catalyst from iodide impurities is minimized, while maintaining desired production parameters. Accordingly, one skilled in the art with the benefit of the present disclosure will be able to select appropriate operating conditions to maintain at least one of water and ethylene oxide, as defined herein, and obtain maximum product selectivity and yield and minimum capital and operational expenditure of guard beds and ethylene oxide reactor.

In a preferred embodiment of the invention, the composition of the recycle gas stream supplied to the guard bed system is controlled such that the concentration of both water and ethylene oxide therein does not exceed the maximum levels as defined herein.

Accordingly, in a preferred embodiment the recycle gas stream comprises (a) no more than 0.6 mol % of water, more preferably no more than 0.59 mol % of water, more preferably no more than 0.55 mol % of water, more preferably no more than 0.5 mol % of water, more preferably no more than 0.4 mol % of water, even more preferably no more than 0.3 mol % of water, yet even more preferably no more than 0.2 mol % of water, most preferably no more than 0.1 mol % of water; and (b) no more than 90 ppmv of ethylene oxide, more preferably no more than 70 ppmv of ethylene oxide, more preferably no more than 50 ppmv of ethylene oxide, more preferably no more than 40 ppmv of ethylene oxide, more preferably no more than 30 ppmv of ethylene oxide, more preferably no more than 20 ppmv of ethylene oxide, even more preferably no more than 15 ppmv of ethylene oxide, yet even more preferably no more than 10 ppmv of ethylene oxide, most preferably no more than 5 ppmv of ethylene oxide, based on the total recycle gas stream supplied to the guard bed system.

In conjunction with controlling the concentration of recycle gas stream components that adversely guard bed capacity at levels as defined herein, the guard beds in the guard bed system are typically designed to have an acceptable, fixed changeout frequency. As mentioned above, from the perspective of both capital and of operating expenditure it is desirable for guard bed changeout frequency to never reach unacceptably high rates.

Within the context of the current invention, this involves adding additional volume of guard bed material (bed sizing) to compensate for expected capacity reductions during commercial operation in comparison to tested reference conditions (e.g. using microreactor and/or pilot plant experiments), within the specific margins for adverse recycle gas components as defined herein, in order to attain a predefined preferred guard bed changeout frequency. Thus, when designing for a certain number of operation days, this allows for the guard beds to stay on line.

The invention is further illustrated by the following Examples.

EXAMPLES

Microreactor Experiments

The influence of the presence of water and ethylene oxide in an ethylene oxidation recycle gas stream on the capacity of silver/alumina guard beds for removing alkyl iodide from said recycle gas stream was investigated using microreactor experiments, wherein an iodide-containing ethylene epoxidation reaction feed gas was directed through a tube of heated guard bed, and outlet gas was monitored periodically for iodide content. These microreactor experiments closely mimic most of the key operational parameters of a commercial unit, including composition of the feed mixture, temperature of the bed, reaction work rate, and pressure.

In all experiments, a ¼" internal diameter stainless steel U-shaped microreactor tube was loaded with 5.27 g of a guard bed material comprising 5% Ag/0.5% K on alumina (Sasol, 1.0 mm, surface area 160 m$^2$/g, bulk packing density 0.76 g/cm$^3$). A feed gas composition was introduced comprising 25 vol % $C_2H_4$/7.5 vol % $O_2$/1.3 vol % $CO_2$/3 ppmv vinyl chloride plus approximately 5000 ppbv methyl iodide and approximately 5000 ppbv ethyl iodide, with nitrogen ballast gas comprising the remainder of the stream.

The effect of ethylene oxide (EO) in the recycle gas stream on iodide capture performance of the guard bed material was investigated by varying the concentration of ethylene oxide added to the feed gas between 0 ppmv, 20 ppmv, 44 ppmv, and 103 ppmv.

The effect of water in the recycle gas stream on iodide capture performance of the guard bed material was investigated by varying the concentration of water added to the feed gas between 0 vol %, 0.3 vol %, and 0.6 vol %.

Performance of the guard bed in capturing iodide from the feed stream was measured as the percentage of guard bed capacity utilized (wherein capture of 1 mmol iodide (I) in the feed gas per 1 mmol silver (Ag) in the guard bed represents 100% capacity utilization) at breakthrough of either ethyl iodide or methyl iodide fed to the guard bed.

FIG. 1 shows the impact of low-level water vapor upon iodide sorption capacity. As can be seen in this figure, water impact is almost linear with a loss of about 10% of iodide adsorption capacity for every 0.3 mol % increase in water in the gas feed.

As an example of the scaling up of pilot plant design to commercial design, it can be seen from the curve displayed in FIG. 1 that a pilot plant water content in the gas feed of, for example 0.1 mol % corresponds to about 96% of stoichiometric alkyl iodide guard bed capacity, while an exemplary 0.5 mol % of water in the recycle gas stream in a commercial plant corresponds to about 84% utilized capacity. The ratio of the two capacities at breakthrough [i.e., 96/84=1.14] is the multiplying factor that needs to be applied to adjust bed size to compensate for the capacity reduction relative to the pilot plant resulting from 0.5 mol % water in the commercial plant guard bed feed gas.

Figure 2:
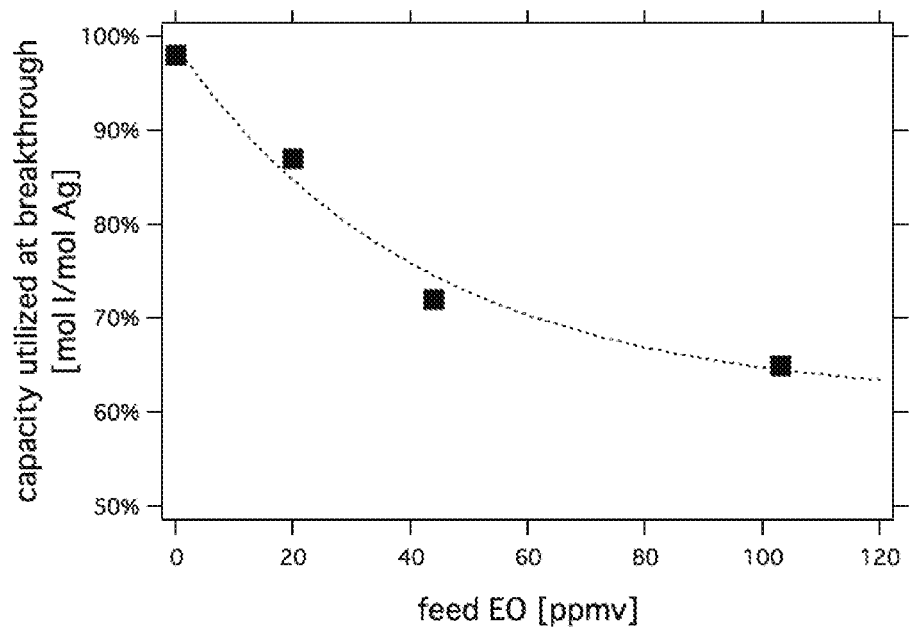
FIG. 2 shows the effect of ethylene oxide in an ethylene epoxidation feed gas stream on the iodide sorption capacity of a silver-based guard bed.

FIG. 2 shows the impact of ethylene oxide in the recycle gas stream on iodide sorption capacity of a silver-based guard bed. As can be seen in this figure, ethylene oxide impact is non-linear with a rapid loss of iodide adsorption capacity even at low levels of ethylene oxide.

As an example of the scaling up of pilot plant design to commercial design, it can be derived from the curve displayed in FIG. 2 that a pilot plant ethylene oxide content in the recycle gas feed of, for example 8 ppmv corresponds to about 88% of stoichiometric alkyl iodide guard bed capacity, while an exemplary 10 ppmv ethylene oxide content in the recycle gas stream in a commercial plant would correspond to about 87% utilized capacity. Accordingly, the multiplying factor that needs to be applied to adjust bed size to compensate for the capacity reduction relative to the pilot plant resulting from 10 ppmv ethylene oxide in the commercial plant guard bed feed gas amounts to 88/87=1.02.

That which is claimed is:

1. A process for producing ethylene glycol and/or ethylene carbonate, said process comprising:

contacting at least a portion of a recycle gas stream comprising an alkyl iodide impurity with a guard bed system positioned upstream of an ethylene oxide reactor to produce a treated recycle gas stream, wherein said guard bed system comprises a guard bed material comprising silver on alumina;

contacting a feed gas stream comprising ethylene, oxygen and at least a portion of the treated recycle gas stream with an epoxidation catalyst in the ethylene oxide reactor to produce an epoxidation reaction product comprising ethylene oxide; and contacting at least a portion of the epoxidation reaction product comprising ethylene oxide with an aqueous absorbent in the presence of an iodide-containing catalyst in an absorber to produce an aqueous product stream comprising ethylene carbonate and/or ethylene glycol and the recycle gas stream comprising the alkyl iodide impurity, wherein the recycle gas stream supplied to the guard bed system comprises (a) 0.1 to 0.59 mol % of water; and/or
(b) 5 to 90 ppmv of ethylene oxide, based on total recycle gas stream supplied to the guard bed system, wherein the water concentration in the recycle gas stream is controlled by one or more of the type of cooling medium, type of cooling apparatus, temperature of the cooling medium, and the amount of cooling medium used to cool the recycle gas stream leaving the absorber, and wherein the ethylene oxide concentration in the recycle gas stream supplied to the guard bed system is controlled by one or more of regulating the concentration of ethylene oxide in the epoxidation reaction product stream, absorber temperature, absorber pressure, catalyst composition, number of absorber trays, shape of absorber trays, absorbent flow, and absorbent composition in the absorber.

2. The process according to claim 1, wherein the recycle gas stream supplied to the guard bed system comprises no more than 0.55 mol % of water.

3. The process according to claim 1, wherein the recycle gas stream supplied to the guard bed system comprises no more than 70 ppmv of ethylene oxide.

4. The process according to claim 1, wherein the recycle gas stream supplied to the guard bed system is further contacted with a second guard bed system comprising a guard bed material capable of removing at least a portion of a vinyl iodide impurity from the recycle gas stream, wherein the treated gaseous feed stream removed from the final guard bed vessel in series of the first guard bed system is supplied as the gaseous feed via a feed line to the second guard bed system.

5. The process according to claim 4, wherein the guard bed material capable of removing at least a portion of a vinyl iodide impurity comprises palladium and gold.

* * * * *